(12) United States Patent
Line

(10) Patent No.: US 11,950,938 B2
(45) Date of Patent: Apr. 9, 2024

(54) HEMOSTAT ORGANIZER

(71) Applicant: TERUMO CARDIOVASCULAR SYSTEMS CORPORATION, Ann Arbor, MI (US)

(72) Inventor: Kevin R. Line, Ann Arbor, MI (US)

(73) Assignee: Terumo Cardiovascular Systems Corporation, Ann Arbor, MI (US)

(*) Notice: Subject to any disclaimer, the term of this patent is extended or adjusted under 35 U.S.C. 154(b) by 260 days.

(21) Appl. No.: 17/227,629

(22) Filed: Apr. 12, 2021

(65) Prior Publication Data

US 2022/0323171 A1 Oct. 13, 2022

(51) Int. Cl.
| | | |
|---|---|---|
| *A61B 50/20* | (2016.01) | |
| *A61B 17/28* | (2006.01) | |
| *B25H 3/04* | (2006.01) | |
| *A61B 17/00* | (2006.01) | |
| *A61B 17/12* | (2006.01) | |

(52) U.S. Cl.
CPC .............. *A61B 50/20* (2016.02); *A61B 17/28* (2013.01); *B25H 3/04* (2013.01); *A61B 2017/00407* (2013.01); *A61B 2017/00438* (2013.01); *A61B 2017/00955* (2013.01); *A61B 2017/12004* (2013.01)

(58) Field of Classification Search
CPC .......... A61B 50/20; A61B 17/28; A61B 50/22
USPC .................................... 206/370; 211/60, 153
See application file for complete search history.

(56) References Cited

U.S. PATENT DOCUMENTS

| | | | | |
|---|---|---|---|---|
| 2,906,410 | A * | 9/1959 | Mcguire ................ | A61B 50/20 D24/228 |
| 3,116,828 | A * | 1/1964 | Glassman .............. | A61B 50/20 D24/229 |
| 3,900,109 | A * | 8/1975 | Peterson ................ | A61B 50/20 422/128 |
| 3,925,014 | A * | 12/1975 | Langdon ................... | A61L 2/26 206/370 |
| 4,512,466 | A * | 4/1985 | Delang .................. | A61B 50/20 206/370 |
| 5,046,624 | A | 9/1991 | Murphy et al. | |
| 5,145,655 | A | 9/1992 | Darlak | |
| 6,426,041 | B1 | 7/2002 | Smith | |

(Continued)

OTHER PUBLICATIONS

Rick Schultz, Hemostats 101: Understanding One of the Most Common Surgical Instruments, Instrument Whisperer, Nov./Dec. 2019.

*Primary Examiner* — Ernesto A Grano
*Assistant Examiner* — Symren K Sanghera
(74) *Attorney, Agent, or Firm* — Fish & Richardson P.C.

(57) ABSTRACT

An organizer is provided for holding surgical forceps in a ready position. Each surgical forceps includes a pair of shanks with distal tips, proximal ring handles, and a ratchet mechanism adjacent the ring handles. The organizer has a base, and a wedge-shaped core projecting upwards along a vertical axis from the base. The core has a profile adapted to fit within a respective opening of each respective forceps bounded by the shanks and the ratchet mechanism when the ratchet mechanisms are engaged. A plurality of wings project radially from the core to define a plurality of substantially U-shaped channels between adjacent wings. The channels are configured to nest the shanks of the forceps so that the respective forceps are locked in the grooves by their respective ratchet mechanisms.

6 Claims, 5 Drawing Sheets

(56) References Cited

U.S. PATENT DOCUMENTS

| | | | |
|---|---|---|---|
| 7,066,328 B2* | 6/2006 | Pulsifer | A61B 50/24 |
| | | | 206/363 |
| 8,505,748 B2 | 8/2013 | Jones et al. | |
| 8,641,984 B2* | 2/2014 | Alston | A61B 50/30 |
| | | | 206/370 |
| 9,179,975 B2* | 11/2015 | Gitman | A61B 50/20 |
| 2004/0206711 A1* | 10/2004 | Hoftman | A61B 50/20 |
| | | | 211/85.13 |
| 2005/0061696 A1 | 3/2005 | Swank | |
| 2009/0152414 A1* | 6/2009 | Lyons | A61B 50/24 |
| | | | 248/176.1 |

* cited by examiner

HEMOSTAT ORGANIZER

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to a tree or tower for holding a plurality of surgical hemostats, and, more specifically, to an organizer for arranging hemostat instruments in a holder from which each hemostat can be easily grasped and removed using the same grip from which the hemostat is to be used.

Many types of surgeries (e.g., cardiovascular surgery) may utilize locking hemostat-type instruments for clamping conduits such as arteries, veins, or tubing of an extracorporeal circulation system. As used herein, "hemostat" means a scissors-like instrument or forceps which can be locked in a closed position or partially closed position to grasp tissue and/or act as a clamp, including for example Kelly forceps, Halsted forceps, Hartman forceps, Crile forceps, Rochester-Pean forceps, Mosquito forceps, sponge forceps, and tube occluding clamps. Important considerations for any sort of surgical interventions include minimizing the surgery time, managing the use of space around the surgical area and within the surgical setting, maintaining sterility, and making surgical instruments easily accessible to user without the awaiting instruments being intrusive.

A hemostat may include a pair of shanks joined where they cross at an intermediate portion along their length by a box lock joint. The distal tips of the shanks provide straight or curved jaws with contacting surfaces that may be serrated or smooth. Ring handles at the proximal ends of the shanks receive a thumb and finger of the user for opening and closing the jaws. A ratchet mechanism is provided between the ring handles to provide a range of locking positions providing a range of potential clamping pressures when the jaws are closed over a particular structure.

For use during a particular surgical event, a supply of hemostats may be set up in a tray, rack, or other retainer to be picked up by a user (e.g., surgeon) as needed. Some trays or racks may have corrugations or slots for holding each forceps vertically so that they are not one atop another, but this requires extra manipulations to pick up and then insert the user's thumb and finger into the ring handles. Furthermore, each separate forceps may be loosely held and subject to being knocked over. Another type of organizer shown in U.S. Pat. No. 4,512,466, issued to Delang, uses upright posts of an organizer to receive the ring handles of a plurality of hemostats which are stored horizontally. The posts are spaced apart such that each of the stored hemostats is in an opened (e.g., unratcheted) position. Thus, each individual hemostat must first be removed from the organizer before it can be grasped in the manner for uses as a hemostat. Furthermore, Delang contemplates that all the stored hemostats have a matching size and shape so that they align with the spacing of the posts and so that they harmoniously lie on top of one another in a stack.

Because of the disadvantages of known organizers, many surgeons simply place the hemostats on a flat surface of nearby equipment or on trays. When lying flat on such a surface, the retrieval and grasping of the hemostat requires time and attention.

SUMMARY OF THE INVENTION

The invention provides an organizer for hemostats/forceps that accepts a range of sizes and shapes, presents successive instruments in an manner for easy grasping via the ring handles by the thumb and finger in an ergonomic orientation which matches the orientation with which the user applies the hemostat/forceps to the patient, and keeps the individual instruments locked in place until deliberately removed from the organizer.

In one aspect of the invention, an organizer is provided for a plurality of surgical forceps, wherein the surgical forceps each includes a pair of shanks with distal tips, proximal ring handles, and a ratchet mechanism adjacent the ring handles. The organizer has a base, and a wedge-shaped core projecting upwards along a vertical axis from the base. The core has a profile adapted to fit within a respective opening of each respective forceps bounded by the shanks and the ratchet mechanism when the ratchet mechanisms are engaged. A plurality of wings project radially from the core to define a plurality of substantially U-shaped channels between adjacent wings. The channels are configured to nest the shanks of the forceps so that the respective forceps are locked in the grooves by their respective ratchet mechanisms.

The organizer is small and unobtrusive, and it allows the hemostats to be aligned in a desired direction and at a height that facilitates an easy motion for grasping and moving a hemostat. Thus, a hand and arm motion of the user is such that a single, fluid movement can be performed in which the user grasps, opens, and removes the hemostat "on the way" toward the intended usage location.

DETAILED DESCRIPTION OF PREFERRED EMBODIMENTS

Figure 1:
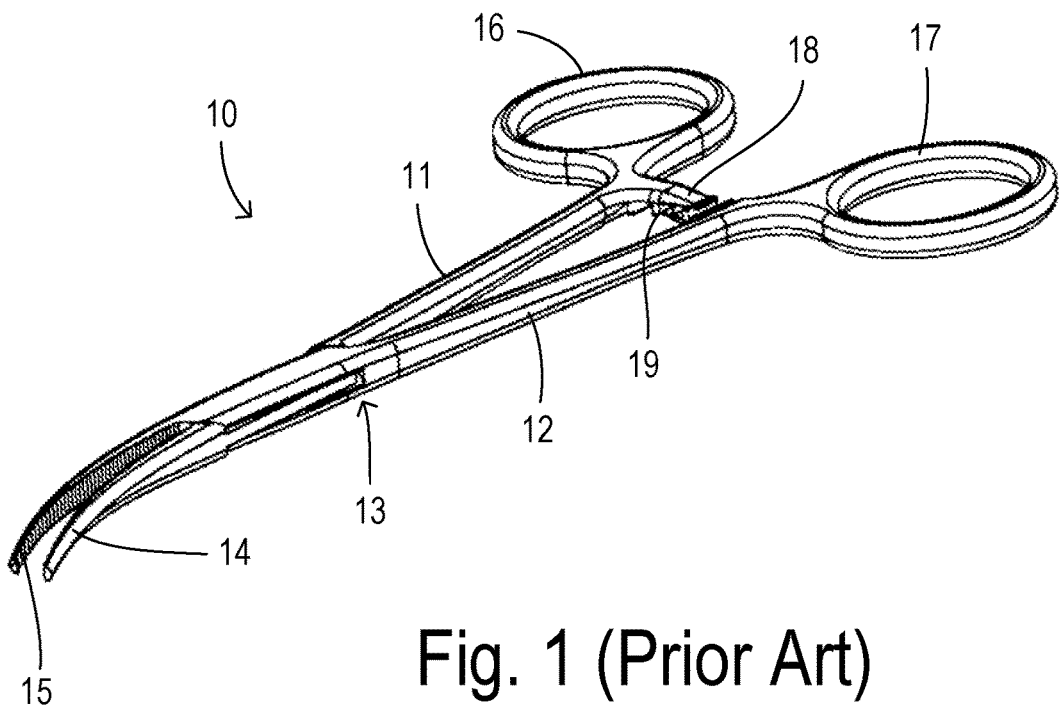
FIG. 1 is a perspective view of a hemostat.

FIG. 1 shows a common type of hemostat 10 with a shank 11 and a shank 12 attached via a box lock 13. Shank 11 has a distal tip 14 and a ring handle 16. Shank 12 has a distal tip 15 and a ring handle 17. Ring handles 16 and 17 include ratchet parts 18 and 19, respectively, of a ratchet mechanism having a plurality of teeth which interact to retain tips 14 and 15 at any one of a plurality of ratchet positions with sufficient force to enable the creation of a desirable clamping pressure. A greater force (which can be easily applied manually by the user) can be used to move the ratchet mechanism is either direction or to open the hemostat completely.

Figure 2:
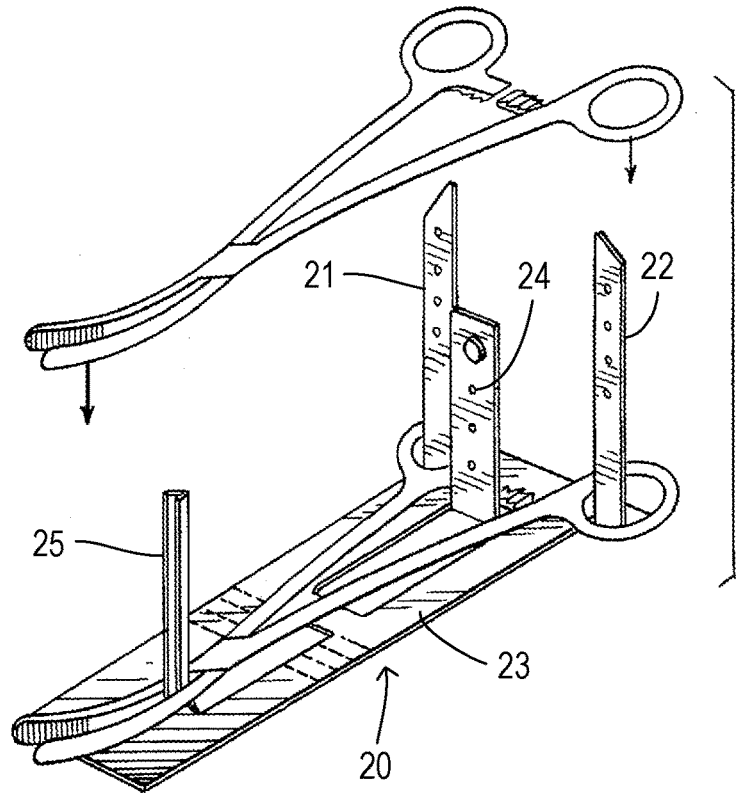
FIG. 2 is a perspective view of a prior art organizer for sterilizing and storing hemostatic instruments.

FIG. 2 shows a prior art organizer 20 in which a pair of posts 21 and 22 extend upward from a cardboard base 23. Finger rings of hemostats are placed over posts 21 and 22. A divider 24 and a separator 25 keep the hemostats in an opened condition. Thus, the hemostats must first be lifted out from the organizer before they can be held in an operative grip (e.g., with thumb and finger through the ring handles). Furthermore, the hemostats are loosely held in place and could be dislodged in the organizer is knocked over.

Figure 3:
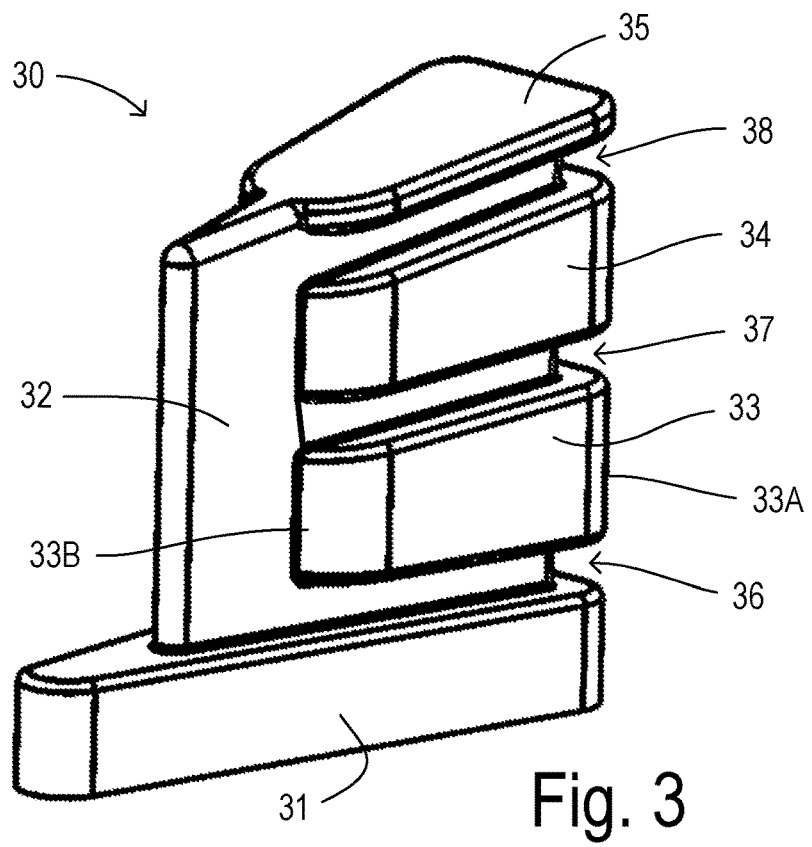
FIG. 3 is a side perspective view of an organizer according to an embodiment of the present invention.

FIG. 3 shows an organizer 30 configured to overcome the drawbacks of conventional organizers. Organizer 30 is preferably comprised of a unitary molded body onto which individual hemostats can be clipped using their ratchet mechanisms. In some preferred embodiments, organizer 30 has a base 31, a wedge-shaped core 32, and a plurality of wings 33, 34, and 35. Core 32 projects upwards along a vertical axis from base 31. The wedge shape of core 32 provides a triangular profile adapted to fit within a respective opening (e.g., a generally triangular opening) of each respective forceps bounded by the shanks and the ratchet mechanism when the ratchet mechanisms are engaged. Wings 33-35 project radially from core 32 and define a plurality of substantially U-shaped channels 36, 37, and 38 between adjacent wings (and/or base 31 and lowest wing 33). Channels 36-38 are configured to nest the shanks of the forceps so that the respective forceps are locked in channels 36-38 by their respective ratchet mechanisms.

Each wing has a proximal end and a distal end (e.g., a proximal end 33A and a distal end 33B of wing 33). The proximal ends of the wings at least partly define portions of the respective channels for receiving respective ratchet mechanisms of the hemostats. Lateral sides of the wings on opposite sides of core 32 define portions of the respective channels that receive the shanks of the hemostats.

Figure 4:
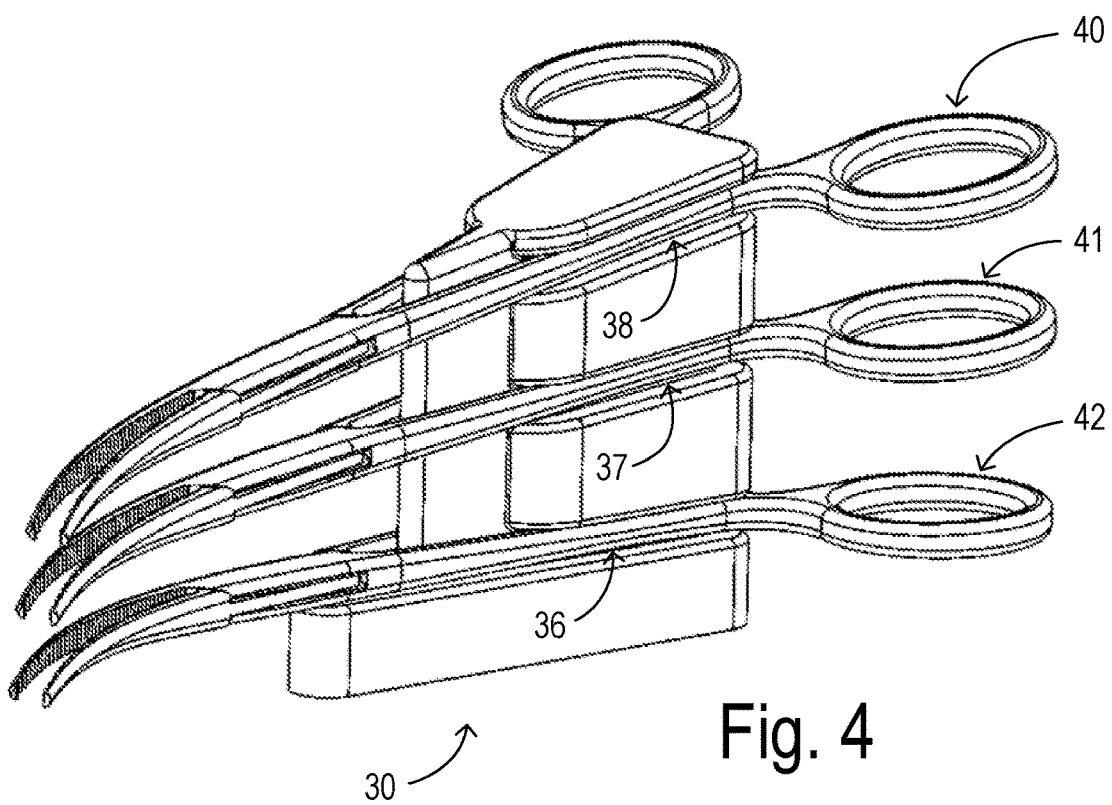
FIG. 4 is a side perspective view of the organizer of FIG. 3 with hemostats loaded into respective channels on the organizer.
Figure 5:
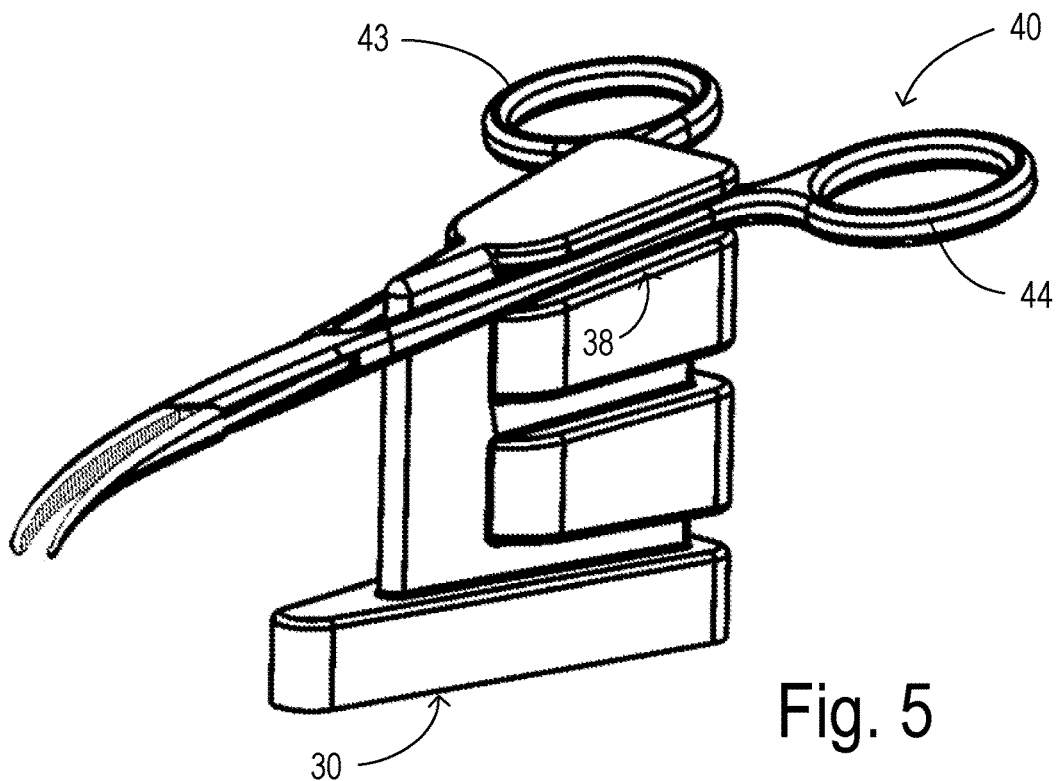
FIGS. 5 and 6 are a perspective view and a vertical cross-sectional view of an organizer with a hemostat loaded in a topmost channel.
Figure 6:
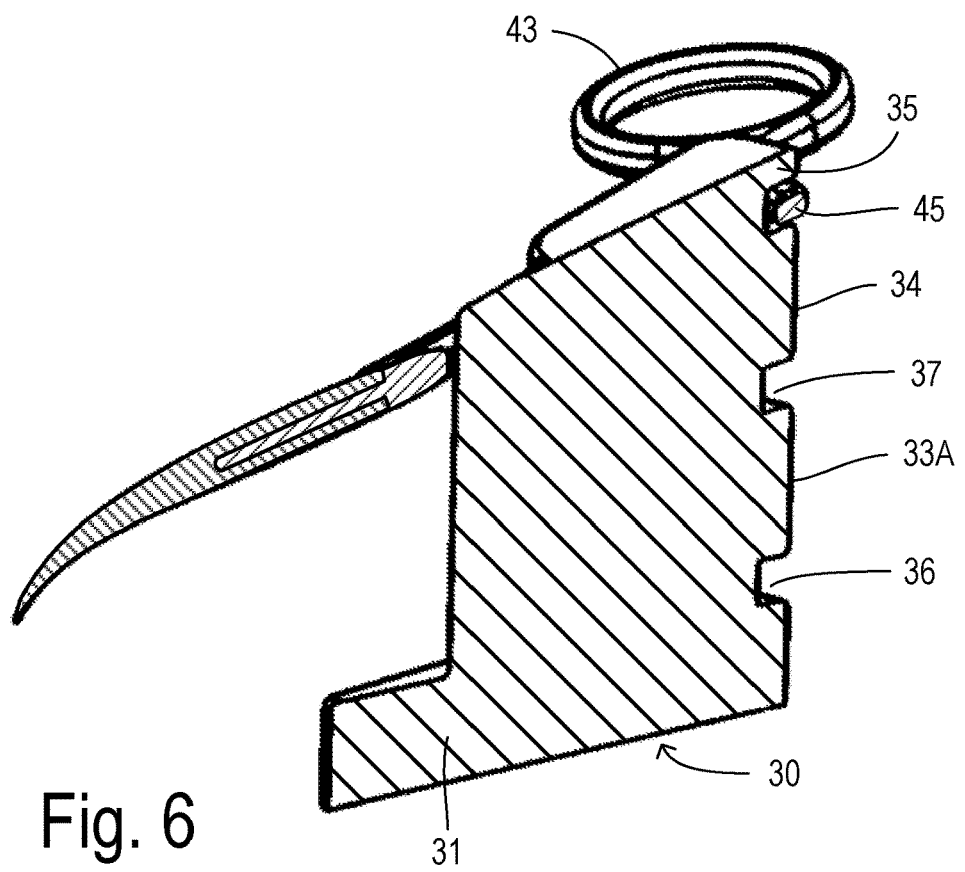

FIG. 4 shows organizer 30 loaded with hemostats 40, 41, and 42, in respective channels 36, 37, and 38. In order to load a hemostat, it is placed into an open state which enlarges the opening between the shanks. Starting with lowest channel, hemostats may be loaded one-by-one. For example, hemostat 42 is guided toward channel 36 and then adjusted toward a closed and locked state with the ratchet mechanism engaged to lock hemostat 42 into the position shown in FIG. 4. After hemostats 41 and 40 are loaded in a similar manner, organizer 30 can be placed at a convenient location for access by a user during a surgical procedure. Organizer 30 can be oriented in a direction the best enables the user to reach for and remove the topmost hemostat. As shown in FIGS. 5 and 6, hemostat 40 can be removed by grasping ring handles 43 and 44, opening hemostat 40 by separating ring handles 43 and 44 to release ratchet mechanism 45 within channel 38, and lifting away from organizer 30 with the hemostat already pointing in the desired direction for use.

Figure 7:
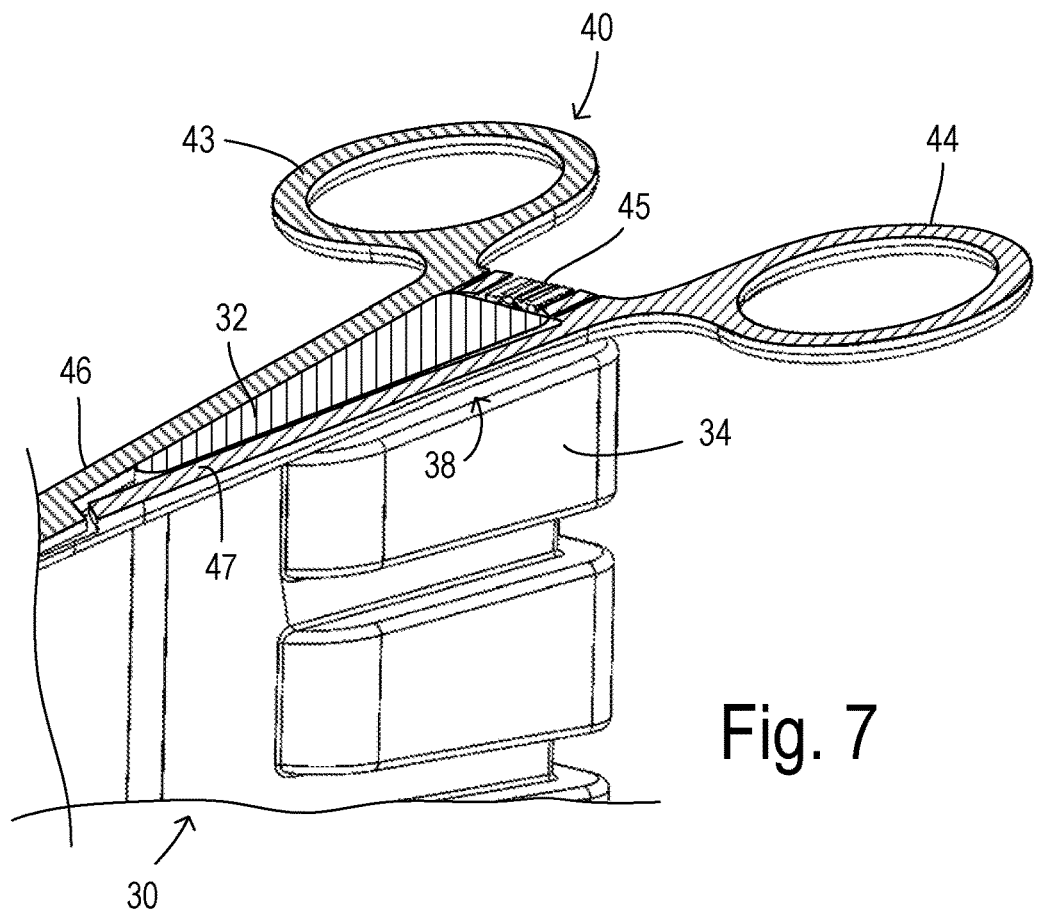
FIG. 7 is a horizontal cross-sectional view of an organizer and hemostat.
Figure 8:
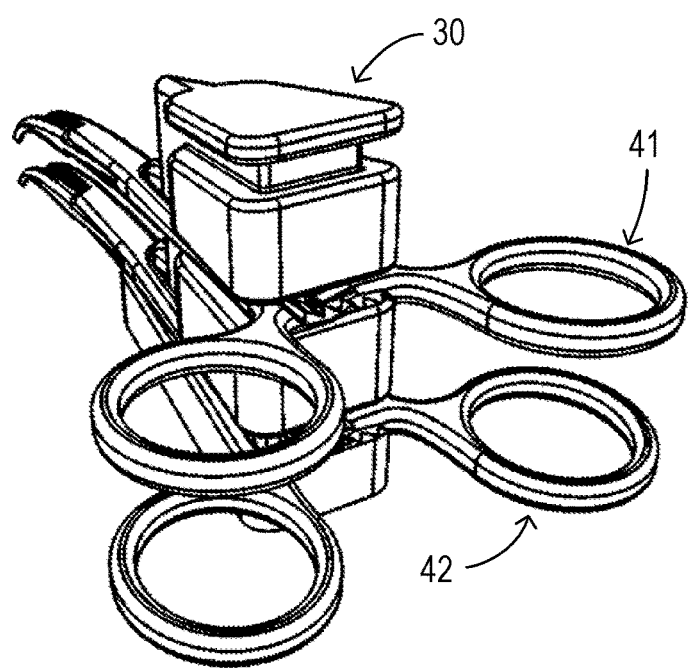
FIG. 8 is a rear perspective view of an organizer with hemostats loaded in lower and middle channels.

FIG. 7 shows a horizontal cross section revealing the placement of hemostat 40 on organizer 30 such that core 32 (partially bounded by channel 38) is received in a triangular opening of hemostat 40 bounded by ratchet mechanism 45 and shanks 46 and 47. Ratchet mechanism 45 and shanks 46 and 47 may rest atop an upper surface of wing 34. As shown in FIG. 8, hemostats 41 and 42 are similarly placed when they are loaded on organizer 30. Although hemostats 40-42 are shown as being identical instruments, hemostats of different sizes and shapes can be loaded onto organizer 30. The particular dimensions of organizer 30 may be selected to accommodate any particular desired set of types and sizes of hemostats that may be desired (e.g., a range of instruments used for particular surgical procedures). In particular, the triangular profile of core 32, the distance between adjacent wings (e.g., the vertical height of the channels), and the lateral extension of the wings (which defines the depths of the channels) can be adjusted to handle a range of sizes and shapes of hemostats. Furthermore, hemostats of different types can be loaded in a sequence from top to bottom of the organizer according to their order of use during a particular surgical procedure, allowing the user to pluck each desired instrument from the top of the stack at the time it is needed.

Figure 9:
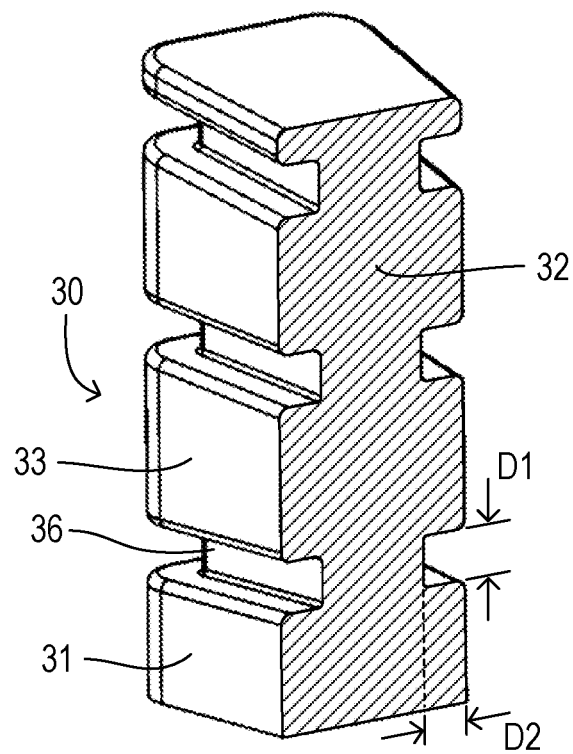
FIG. 9 is a vertical cross section of the organizer of FIG. 3.

FIG. 9 shows a vertical cross section of organizer 30. A separation of base 31 and wing 33 provides channel 36 with a vertical height distance D1. A lateral extension of wing 33 and base 31 from core 32 provides channel 36 with a depth D2. The resulting channel size is configured to accommodate the shanks and ratchet mechanisms of selected hemostats or other forceps.

In one preferred embodiment, the hemostats/forceps may be tilted forward (e.g., by providing the channels with a downward slant from the handles) so that the distal tips are generally lower than the proximal ring handles. This locates the distal tips close together is a compact grouping that is easier to manage and to keep out of the way. It also provides additional space between the ring handles of adjacent hemostats for easier manipulation to open and remove the topmost instrument. In some embodiments, the forward tilt is obtained by arranging the wings such that each proximal end of a respective wing has a vertical height which is greater than a vertical height of the distal end of the respective wing.

Figure 10:
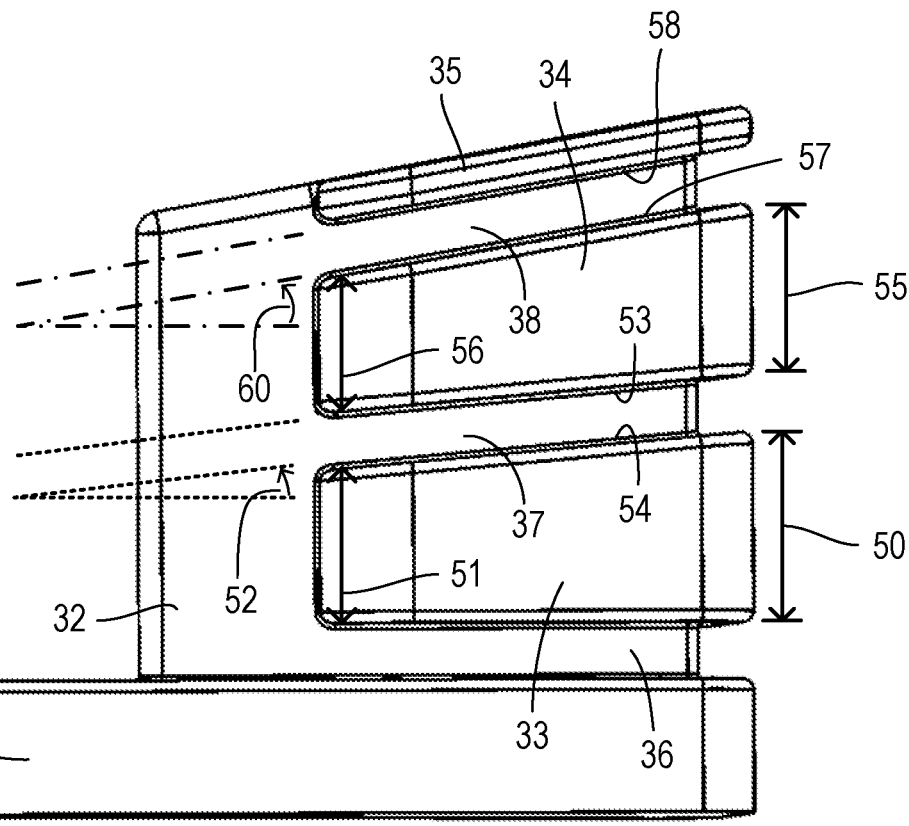
FIG. 10 is a side view of the organizer of FIG. 3 showing progressive changes in a slant of the channels for receiving the hemostats.

As shown in FIG. 10, channel 36 is generally horizontal. A bottom side of lowermost wing 33 is also generally horizontal so that the sides of channel 36 are parallel. Wing 33 has a proximal end height 50 which is greater than a distal end height 51, resulting in channel 37 having a lower surface 54 having a downward slant from the proximal end to the distal end. Wing 34 has a surface 53 which defines a top surface of channel 37 which is parallel with surface 54. Consequently, channel 37 has an inclination angle 52. The slope of channel 37 has an inclination angle which is preferably in a range from about 3° to about 10°, and which is most preferably about 50.

In some embodiments, the slanted channels have respective inclination angles that are progressively greater from a lowest slanted channel to a highest slanted channel. The progression may utilize an angle increment which may be in a range from about 3° to about 10°, and most preferably about 5°. In FIG. 10, wing 34 has a proximal end height 55 which is greater than a distal end height 56, resulting in channel 38 having a lower surface 57 having an even larger downward slant from its proximal end to its distal end than the slope of channel 37. Wing 35 has a surface 58 which defines a top surface of channel 38 which is parallel with surface 57. Channel 38 has an inclination angle 60 which is greater than inclination angle 52. For example, inclination angle 60 may be twice as large as inclination angle 52 (e.g., angle 52 being about 5° and angle 60 being about 10°). For a taller tower with a third channel, the inclination angle for the third channel may increase according to a fixed incremental angle (e.g. an increment of 5° resulting in an inclination of about 15°) or by an increment following a different progression.

For a taller tower with an even greater number of hemostat channels, it may be desirable to progressively increase the inclination angles at a slower rate (e.g., using a smaller incremental angle).

What is claimed is:

1. An organizer for a plurality of surgical forceps, wherein each forceps of the plurality of surgical forceps includes a pair of shanks with distal tips, proximal ring handles, and a ratchet mechanism adjacent the ring handles, the pair of shanks and the ratchet mechanism bounding an opening defined by the forceps when the ratchet mechanism is engaged, the organizer comprising:
   a base;
   a wedge-shaped core projecting upwards along a vertical axis from the base and having a profile adapted to fit within the respective opening of each forceps of a plurality of forceps; and
   a plurality of wings projecting radially from the core and defining a plurality of substantially U-shaped channels between adjacent wings, wherein the channels are configured to nest the shanks of the forceps so that the respective forceps are locked in the channels by their respective ratchet mechanisms;
   wherein at least some of the channels are slanted downward from a respective proximal end to a respective distal end so that the ring handles of corresponding forceps are higher than the corresponding distal tips; and
   wherein the slanted channels have respective inclination angles that are progressively greater from a lowest slanted channel to a highest slanted channel.

2. The organizer of claim 1 wherein each wing has a proximal end and a distal end, wherein the proximal ends of the wings at least partly define portions of the channels for receiving respective ratchet mechanisms, and wherein each proximal end of a respective wing has a vertical height which is greater than a vertical height of the distal end of the respective wing.

3. The organizer of claim 1 wherein the inclination angles between adjacent slanted channels progressively increase according to an increment in a range of 3° to 10°.

4. The organizer of claim 3 wherein the increment is about 5°.

5. The organizer of claim 1 wherein the surgical forceps are comprised of hemostat instruments.

6. The organizer of claim 1 wherein the base, core, and wings are formed by a unitary body comprised of molded thermoplastic.

* * * * *